US006610282B1

(12) United States Patent
Ghosh

(10) Patent No.: US 6,610,282 B1
(45) Date of Patent: Aug. 26, 2003

(54) POLYMERIC CONTROLLED RELEASE COMPOSITIONS

(75) Inventor: Tirthankar Ghosh, Oreland, PA (US)

(73) Assignee: Rohm and Haas Company, Philadelphia, PA (US)

(*) Notice: Subject to any disclaimer, the term of this patent is extended or adjusted under 35 U.S.C. 154(b) by 0 days.

(21) Appl. No.: 09/291,780

(22) Filed: Apr. 14, 1999

Related U.S. Application Data

(60) Provisional application No. 60/084,317, filed on May 5, 1998.

(51) Int. Cl.[7] ............................................... H01N 25/10
(52) U.S. Cl. ................ 424/78.09; 424/76.8; 424/78.07; 424/78.31; 424/78.36; 424/405; 424/408; 424/409; 424/411; 424/413; 424/486; 514/372; 514/373; 514/478; 514/492; 514/525; 523/122; 523/132
(58) Field of Search ................................ 523/122, 132; 424/405, 408, 409, 411, 413, 78.09, 78.18, 78.31, 401, 486, 78.36, 78.07; 514/372, 373, 492, 478, 479, 525

(56) References Cited

U.S. PATENT DOCUMENTS

| 4,031,055 A | | 6/1977 | Dupont et al. | |
|---|---|---|---|---|
| 4,729,834 A | | 3/1988 | Nakagawa et al. | |
| 4,996,220 A | * | 2/1991 | Sehraua et al. | 514/372 |
| 5,364,977 A | | 11/1994 | Asai et al. | 568/720 |

FOREIGN PATENT DOCUMENTS

| EP | 0523957 | * | 1/1993 |
|---|---|---|---|
| EP | 0709358 A1 | | 5/1996 |
| EP | 0 880 892 | | 2/1998 |
| GB | 2072508 | * | 2/1981 |
| JP | 43001759 | * | 11/1968 |
| WO | WO 96/00251 | | 1/1996 |
| WO | WO 97/03657 | | 2/1997 |
| WO | WO 97/16463 | | 5/1997 |

OTHER PUBLICATIONS

U.S. patent application Ser. No. 09/073,282, Ghosh et al., filed May 6, 1998.

"Two Stereoisomeric Macrocyclic Resorcinol–Acetaldehyde Condensation Products"; A. G. Sverker Hogberg; J. Org. Chem. 1980, 45, pp. 4498–4500.

"Stereoselective Synthesis and DNMR Study of Two 1,8, 15,22–Tetraphenyl[1_4]metacyclophan–3,5,10,12,17,19,24, 26–octols[1,2]", A. G. Sverker Hogberg; J. Am. Chem. Soc. 1980, 102, pp. 6046–6050.

Host–Guest Complexation. 48, Octol Building Blocks for Cavitanda and Carcerands; Linda M. Tunstad, John A. Tucker, Enrico Dalcanale, Jurgen Weiser, Judi A. Bryant, John C. Sherman, Roger C. Helgeson, Carolyn B. Knobler, and Donald J. Cram; J. Org. Chem., 1989, 54, pp. 1305–1312.

* cited by examiner

Primary Examiner—Neil S. Levy
(74) Attorney, Agent, or Firm—S. Matthew Cairns; Stephen E. Johnson

(57) ABSTRACT

Disclosed are compositions containing biologically active compounds that slowly release the biologically active compound. These compositions may be directly incorporated into the locus to be protected or may be applied to a structure in a coating.

18 Claims, No Drawings

POLYMERIC CONTROLLED RELEASE COMPOSITIONS

This application claims the benefit of Provisional application 60/084,317 filed May 5, 1998.

BACKGROUND OF THE INVENTION

This invention relates generally to a composition for controlling the release of biologically active compounds. In particular, this invention relates to the use of certain hydroxystyrene polymers to control the release of biologically active compounds.

The ability to control release of biologically active compounds to a locus to be protected is important in the field of biologically active compounds. Typically, when a biologically active compound is added to a locus to be protected, the compound is rapidly released, whether or not it is needed. Controlled release compositions deliver the biologically active compound in a manner that more closely matches the need for the compound. In this way, only the amount of the biologically active compound needed is released into the locus to be protected. Controlled release offers the advantages of reduced cost, lowered toxicity and increased efficiency.

Various methods of controlled release are known. Such methods include encapsulation of the biologically active compound, adsorption of the biologically active compound on an inert carrier, such as silica gel, and clathration of the biologically active compound.

All of these methods have drawbacks to widespread commercial use, such as expensive starting materials, limited compatibility of the controlled release method to the compounds to be released or locus to be protected, and limited control of the release of the biologically active compounds. For example, whether a clathrate forms is solvent dependent, which limits available solvent choices. An additional problem with clathrates is that solvent, rather than the desired biologically active compound, is sometimes incorporated into the complex.

For example, EP 709 358 A (Suzuki et al.) discloses a clathrate of isothiazolones using a tetrakisphenol compound. Although these compositions provide some control of the release of the isothiazolone, the amount of control is limited and the tetrakisphenol compound used to prepare the clathrate is very expensive. Suzuki et al. do not discuss hydroxystyrene polymers.

Ghosh et al. (U.S. Ser. No. 60/047,966) disclose controlled release compositions of certain polyphenolic compounds and biologically active compounds. Ghosh et al. do not discuss hydroxystyrene polymers.

There is therefore a continuing need for controlled release biologically active compositions that are inexpensive, compatible in a broad range of loci to be protected, and more effective at controlling the release of the biologically active compound than compositions currently available.

SUMMARY OF THE INVENTION

The present invention is directed to a controlled release composition comprising a biologically active compound and a hydroxystyrene polymer.

The present invention is also directed to a method of controlling or inhibiting the growth of microorganisms in a locus comprising introducing into or onto the locus to be protected an effective amount of the composition described above.

The present invention is further directed to a method of eliminating or inhibiting the growth of marine organisms on a structure comprising introducing into or onto the structure to be protected an effective amount of the composition described above.

The present invention is further directed to a method of eliminating or inhibiting the growth of fungi, plants and insects comprising introducing into or onto the locus to be protected an effective amount of the composition described above.

DETAILED DESCRIPTION OF THE INVENTION

As used throughout the specification, the following terms shall have the following meanings, unless the context clearly indicates otherwise.

As used herein, the term "hydroxystyrene polymer" means both hydroxystyrene homopolymers and hydroxystyrene copolymers. The term "alkyl (meth)acrylate" refers to either the corresponding acrylate or methacrylate ester; similarly, the term "(meth)acrylic" refers to either the corresponding acrylic or methacrylic acid and derivatives. "Alkyl" means ($C_1$–$C_{30}$) alkyl. "Copolymer" or "copolymer material" refers to polymer compositions containing units of hydroxystyrene and one or more other monomers or monomer types. "Monomer type" refers to those monomers that represent mixtures of individual closely related monomers, for example, LMA (mixture of lauryl and myristyl methacrylates), DPMA (a mixture of dodecyl, tridecyl, tetradecyl and pentadecyl methacrylates), SMA (mixture of hexadecyl and octadecyl methacrylates), CEMA (mixture of hexadecyl, octadecyl and eicosyl methacrylates). For the purposes of the present invention, each of these mixtures represents a single monomer or "monomer type" when describing monomer ratios and copolymer compositions. The term "halo" or "halogen" means fluorine, chlorine, bromine, or iodine.

The term "biologically active compounds" refers to microbicides, marine antifouling agents, and agricultural pesticides. "Microbicide" refers to a compound capable of inhibiting the growth of or controlling the growth of microorganisms at a locus. The term "microorganism" includes, but is not limited to, fungi, bacteria, and algae.

"Marine antifouling agent" includes algaecides and molluscicides. "Marine antifouling activity" is intended to include both the elimination of and inhibition of growth of marine organisms. Marine organisms controlled by marine antifouling agents suitable for use in this invention include both hard and soft fouling organisms. Generally speaking, the term "soft fouling organisms" refers to plants and invertebrates, such as slime, algae, kelp, soft corals, tunicates, hydroids, sponges, and anemones, while the term "hard fouling organisms" refers to invertebrates having some type of hard outer shell, such as barnacles, tubeworms, and molluscs.

"Agricultural pesticides" include agricultural fungicides, herbicides and insecticides. "Agricultural fungicide" refers to a compound capable of inhibiting the growth of or controlling the growth of fungi in an agricultural application, such as treatment of plants and soil; "herbicide" refers to a compound capable of inhibiting the growth of or controlling the growth of certain plants; and "insecticide" refers to a compound capable of controlling insects.

All amounts are percent by weight ("%wt") based on total weight of polymer or composition involved, unless otherwise noted and all %wt ranges are inclusive. Molecular weights of the hydroxystyrene polymers refer to the weight average molecular weights, unless otherwise specified. As used throughout the specification, the following abbreviations are applied: mg=milligram; mL=milliliter; L=liter; HPLC=high performance liquid chromatography; $M_w$=weight average molecular weight; $M_n$=number average molecular weight; and ppm=parts per million.

The biologically active compounds useful in this invention are those which are hydrogen bond acceptors. That is, the compounds are those having one or more atoms selected from nitrogen, oxygen, fluorine or mixtures thereof. The nitrogen or oxygen may have single or multiple bonds, such as in a carbonyl, imine, nitrile, hydroxy, amide, alkoxy, ester, ether or amine group.

Suitable microbicides of the present invention include, but are not limited to: 5-chloro-2-methyl-3-isothiazolone; 2-methyl-3-isothiazolone; 2-n-octyl-3-isothiazolone; 4,5-dichloro-2-n-octyl-3-isothiazolone; 3-iodo-2-propynyl butyl carbamate; 1,2-dibromo-2,4-dicyanobutane; methylene-bis-thiocyanate; 2-thiocyanomethylthiobenzothiazole; tetrachloroisophthalonitrile; 5-bromo-5-nitro-1,3-dioxane; 2-bromo-2-nitropropanediol; 2,2-dibromo-3-nitrilopropionamide; N,N'-dimethylhydroxyl-5,5'-dimethylhydantoin; bromochlorodimethylhydantoin; 1,2-benzisothiazolin-3-one; 4,5-trimethylene-2-methyl-3-isothiazolone; 5-chloro-2-(2,4-dichlorophenoxy)phenol and 3,4,4'-trichlorocarbanilide.

Suitable marine antifouling agents of the present invention include, but are not limited to: manganese ethylenebisdithiocarbamate; zinc dimethyl dithiocarbamate; 2-methyl-4-t-butylamino-6-cyclopropylamino-s-triazine; 2,4,5,6-tetrachloroisophthalonitrile; N,N-dimethyl dichlorophenyl urea; zinc ethylenebisdithiocarbamate; copper thiocyanate; 4,5-dichloro-2-n-octyl-3-isothiazolone; N-(fluorodichloromethylthio)-phthalimide; N,N-dimethyl-N'-phenyl-N'-fluorodichloromethylthio-sulfamide; zinc 2-pyridinethiol-1-oxide; tetramethylthiuram disulfide; 2,4,6-trichlorophenylmaleimide; 2,3,5,6-tetrachloro-4-(methylsulfonyl)-pyridine; 3-iodo-2-propynyl butyl carbamate; diiodomethyl p-tolyl sulfone; bis dimethyl dithiocarbamoyl zinc ethylenebisdithiocarbamate; phenyl (bispyridil)bismuth dichloride; 2-(4-thiazolyl)-benzimidazole; pyridine triphenyl borane; phenylamides; halopropargyl compounds; or 2-haloalkoxyaryl-3-isothiazolones. Suitable 2-haloalkoxyaryl-3-isothiazolones include, but are not limited to, 2-(4-trifluoromethoxyphenyl)-3-isothiazolone, 2-(4-trifluoromethoxyphenyl)-5-chloro-3-isothiazolone, and 2-(4-trifluoromethoxyphenyl)-4,5-dichloro-3-isothiazolone.

Suitable agricultural fungicides of the present invention include, but are not limited to: dithiocarbamate and derivatives such as ferbam, ziram, maneb, mancozeb, zineb, propineb, metham, thiram, the complex of zineb and polyethylene thiuram disulfide, dazomet, and mixtures of these with copper salts; nitrophenol derivatives such as dinocap, binapacryl, and 2-sec-butyl-4,6-dinitrophenyl isopropyl carbonate; heterocyclic structures such as captan folpet, glyodine, dithianon, thioquinox, benomyl, thiabendazole, vinolozolin, iprodione, procymidone, triadimenol, triadimefon, bitertanol, fluoroimide, triarimol, cycloheximide, ethirimol, dodemorph, dimethomorph, thifluzamide, and, quinomethionate; miscellaneous halogenated fungicides such as: chloranil, dichlone, chloroneb, tricamba, dichloran, and polychloronitrobenzenes; fungicidal antibiotics such as: griseofulvin, kasugamycin and streptomycin; miscellaneous fungicides such as: diphenyl sulfone, dodine, methoxyl, 1-thiocyano-2,4-dinitrobenzene, 1-phenylthiosemicarbazide, thiophanate-methyl, and cymoxanil; as well as acylalanines such as, furalaxyl, cyprofuram, ofurace, benalaxyl, and oxadixyl; fluazinam, flumetover, phenylbenzamide derivatives such as those disclosed in EP 578586 A1, amino acid derivatives such as valine derivatives disclosed in EP 550788 A1, methoxyacrylates such as methyl (E)-2-(2-(6-(2-cyanophenoxy)pyrimidin-4-yloxy)phenyl)-3-methoxyacrylate; benzo(1,2,3)thiadiazole-7-carbothioic acid S-methyl ester: propamocarb; imazalil; carbendazim; myclobutanil; fenbuconazole; tridemorph; pyrazophos; fenarimol; fenpiclonil; and pyrimethanil.

Suitable herbicides of the present invention include, but are not limited to: carboxylic acid derivatives, including benzoic acids and their salts; phenoxy and phenyl substituted carboxylic acids and their salts; and trichloroacetic acid and its salts; carbamic acid derivatives, including ethyl N,N-di(n-propyl)thiolcarbamate and pronamide; substituted ureas, substituted triazines, diphenyl ether derivatives such as oxyfluorfen and fluoroglycofen, anilides such as propanil, oxyphenoxy herbicides, uracils, nitriles, and other organic herbicides such as dithiopy and, thiazopyr.

Suitable insecticides of the present invention include, but are not limited to: acephate; aldicarb; alpha-cypermethrin; azinphos-methyl; bifenthrin; binapacryl; buprofezin; carbaryl; carbofuran; cartap; chlorpyrifos; chlorpyrifos methyl; clofentezine; cyfluthrin; cyhexatin; cypermethrin; cyphenothrin; deltamethrin; demeton; demeton-Smethyl; demeton-O-methyl; demeton-S; demeton-S-methyl sulfoxid; demephion-O; demephion-S; dialifor; diazinon; dicofol; dicrotophos; diflubenzuron; dimethoate; dinocap; endosulfan; endothion; esfenvalerate; ethiofencarb; ethion; ethoate-methyl; ethoprop; etrimfos; fenamiphos; fenazaflor; fenbutatin-oxide; fenitrothion; fenoxycarb; fensulfothion; fenthion; fenvalerate; flucycloxuron; flufenoxuron; fluvalinate; fonofos; fosmethilan; furathiocarb; hexythiazox; isazophos; isofenphos; isoxathion; methamidophos; methidathion; methiocarb; methomyl; methyl parathion; mevinphos; mexacarbate; monocrotophos; nicotine; omethoate; oxamyl; parathion; permethrin; phorate; phosalone; phosmet; phosphamidon; pirimicarb; pirimiphosethyl; profenofos; promecarb; propargite; pyridaben; resmethrin; rotenone; tebufenozide; temephos; TEPP; terbufos; thiodicarb; tolclofos-methyl; triazamate; triazophos and vamidothion.

The biologically active compound is preferably a microbicide or a marine antifouling agent. Especially preferred are 2-methyl-3-isothiazolone, 5-chloro-2-methyl-3-isothiazolone, 2-n-octyl-3-isothiazolone, 4,5-dichloro-2-n-octyl-3-isothiazolone, benzisothiazolone, 4,5-trimethylene-3-isothiazolone, 3-iodo-2-propynyl butyl carbamate; 5-chloro-2-(2,4-dichlorophenoxy)phenol and 3,4,4'-trichlorocarbanilide.

Any hydroxystyrene homopolymer or copolymer is useful in the present invention. Suitable hydroxystyrene homopolymers include, but are not limited to: hydroxystyrene homopolymer, hydroxy methylstyrene homopolymer, and halohydroxystyrene homopolymer, such as bromohydroxystyrene homopolymer and chlorohydroxystyrene homopolymer. Preferably, the hydroxystyrene homopolymers have a molecular weight in the range of 1,000 to 100,000, and more preferably in the range of 2,000 to 50,000, and most preferably in the range of 4,000 to 25,000.

Hydroxystyrene copolymers useful in the present invention are copolymers of hydroxystyrene with one or more comonomers. Any comonomer that can be copolymerized with hydroxystyrene may be used to prepare the copolymers useful in the present invention. The comonomers useful in the present invention can be monoethylenically or polyethylenically unsaturated. Preferably the comonomers are monoethylenically unsaturated monomers. Polyethylenically unsaturated comonomers which lead to crosslinking during the polymerization could be useful for compositionsrequiring even more control of the release of the biologically active molecules. Polyethylenically unsaturated monomers which do not lead to crosslinking or only crosslink to a small degree, for example, butadiene, are also satisfactory comonomers.

Suitable monoethylenically unsaturated monomers include, but are not limited to: vinylaromatic monomers, nitrogen-containing ring compounds, ethylene and substituted ethylene monomers.

Suitable vinylaromatic monomers include, but are not limited to: styrene, α-methylstyrene, vinyltoluene, ortho-, meta- and para-methylstyrene, ethylvinylbenzene, vinylnaphthalene and vinylxylenes. The vinylaromatic monomers can also include their corresponding substituted counterparts, for example, halogenated derivatives, that is, containing one or more halogen groups, such as fluorine, chlorine or bromine; and nitro, cyano, alkoxy, haloalkyl, carbalkoxy, carboxy, amino and alkylamino derivatives. Styrene and halogenated styrene monomers are preferred.

Suitable nitrogen-containing ring compounds include, but are not limited to: vinylpyridine, 2-methyl-5-vinylpyridine, 2-ethyl-5-vinylpyridine, 3-methyl-5-vinylpyridine, 2,3-dimethyl-5-vinylpyridine, 2-methyl-3-ethyl-5-vinylpyridine, methyl-substituted quinolines and isoquinolines, 1-vinylimidazole, 2-methyl-1-vinylimidazole, N-vinylcapro-lactam, N-vinylbutyrolactam and N-vinylpyrrolidone.

Suitable ethylene and substituted ethylene monomers include, but are not limited to: for example: α-olefins such as propylene, isobutylene and long chain alkyl α-olefins (such as ($C_{10}$–$C_{20}$)alkyl α-olefins); vinyl alcohol esters such as vinyl acetate and vinyl stearate; vinyl halides such as vinyl chloride, vinyl fluoride, vinyl bromide, vinylidene chloride, vinylidene fluoride and vinylidene bromide; vinyl nitriles such as acrylonitrile and methacrylonitrile; (meth) acrylic acid and derivatives such as corresponding amides and esters; maleic acid and derivatives such as corresponding anhydride, amides and esters; fumaric acid and derivatives such as corresponding amides and esters; itaconic and citraconic acids and derivatives such as corresponding anhydrides, amides and esters.

A preferred class of (meth)acrylic acid derivatives is represented by alkyl (meth)acrylate, substituted (meth) acrylate and substituted (meth)acrylamide monomers. Each of the monomers can be a single monomer or a mixture having different numbers of carbon atoms in the alkyl portion. Preferably, the monomers are selected from the group consisting of ($C_1$–$C_{24}$)alkyl (meth)acrylates, hydroxy ($C_2$–$C_6$)alkyl (meth)acrylates, dialkylamino($C_2$–$C_6$)alkyl (meth)acrylates and dialkylamino($C_2$–$C_6$)alkyl (meth) acrylamides. The alkyl portion of each monomer can be linear or branched. Preferably, the hydroxy($C_2$–$C_6$)alkyl (meth)acrylate is hydroxyethyl methacrylate (HEMA).

Particularly preferred monomers useful in the copolymers of the present invention are the alkyl (meth)acrylates. Examples of the alkyl (meth)acrylate monomer where the alkyl group contains from 1 to 6 carbon atoms (also called the "low-cut" alkyl (meth)acrylates), are methyl methacrylate (MMA), methyl and ethyl acrylate, propyl methacrylate, butyl methacrylate (BMA) and butyl acrylate (BA), isobutyl methacrylate (IBMA), hexyl methacrylate and cyclohexyl methacrylate, cyclohexyl acrylate and combinations thereof Preferred low-cut alkyl methacrylates are methyl methacrylate and butyl methacrylate.

Examples of the alkyl (meth)acrylate monomer where the alkyl group contains from 7 to 15 carbon atoms (also called the "mid-cut" alkyl (meth)acrylates), are 2-ethylhexyl acrylate (EHA), 2-ethylhexyl methacrylate, octyl methacrylate, decyl methacrylate, isodecyl methacrylate (IDMA, based on branched ($C_{10}$)alkyl isomer mixture), undecyl methacrylate, dodecyl methacrylate (also known as lauryl methacrylate), tridecyl methacrylate, tetradecyl methacrylate (also known as myristyl methacrylate), pentadecyl methacrylate and combinations thereof. Also useful are: dodecyl-pentadecyl methacrylate (DPMA), a mixture of linear and branched isomers of dodecyl, tridecyl, tetradecyl and pentadecyl methacrylates; and lauryl-myristyl methacrylate (LMA), a mixture of dodecyl and tetradecyl methacrylates. The preferred mid-cut alkyl methacrylates are lauryl-myristyl methacrylate, dodecyl-pentadecyl methacrylate and isodecyl methacrylate.

Examples of the alkyl (meth)acrylate monomer where the alkyl group contains from 16 to 24 carbon atoms (also called the "high-cut" alkyl (meth)acrylates), are hexadecyl methacrylate (also known as cetyl methacrylate), heptadecyl methacrylate, octadecyl methacrylate (also known as stearyl methacrylate), nonadecyl methacrylate, eicosyl methacrylate, behenyl methacrylate and combinations thereof Also useful are: cetyl-eicosyl methacrylate (CEMA), a mixture of hexadecyl, octadecyl, and eicosyl methacrylate; and cetyl-stearyl methacrylate (SMA), a mixture of hexadecyl and octadecyl methacrylate. The preferred high-cut alkyl methacrylates are cetyl-eicosyl methacrylate and cetyl-stearyl methacrylate.

The mid-cut and high-cut alkyl (meth)acrylate monomers described above are generally prepared by standard esterification procedures using technical grades of long chain aliphatic alcohols, and these commercially available alcohols are mixtures of alcohols of varying chain lengths containing between 10 and 15 or 16 and 20 carbon atoms in the alkyl group. Consequently, for the purposes of this invention, alkyl (meth)acrylate is intended to include not only the individual alkyl (meth)acrylate product named, but also to include mixtures of the alkyl (meth)acrylates with a predominant amount of the particular alkyl (meth)acrylate named. The use of these commercially available alcohol mixtures to prepare (meth)acrylate esters results in the LMA, DPMA, SMA and CEMA monomer types described above. Preferred (meth)acrylic acid derivatives useful in the process of the present invention are methyl methacrylate, butyl methacrylate, isodecyl methacrylate, lauryl-myristyl methacrylate, dodecyl-pentadecyl methacrylate, cetyl-eicosyl methacrylate and cetyl-stearyl methacrylate.

Particularly useful in the present invention is a hydroxystyrene block copolymer prepared by polymerizing hydroxystyrene polymers with formaldehyde and a polyphenolic compound, such as those disclosed in Ghosh et al. (U.S. Ser. No. 60/047,966), herein incorporated by reference to the extent that it teaches how to prepare these polyphenolic compounds. It is preferred that the hydroxystyrene polymer used to prepare these block copolymers be a homopolymer.

In the hydroxystyrene copolymers useful in the present invention the weight ratio of hydroxystyrene monomer to comonomer is in the range of 99:1 to 1:99. It is preferred that the weight ratio be in the range of 90:10 to 10:90, more preferably 15:85 to 70:30.

Particularly preferred hydroxystyrene polymers useful in the present invention are hydroxystyrene homopolymer, brominated hydroxystyrene homopolymer, hydroxystyrene/ styrene copolymer, hydroxystyrene/MMA copolymer, hydroxystyrene/BA copolymer, and hydroxystyrene/HEMA copolymer.

The hydroxystyrene homopolymers and copolymers useful in the present invention are generally commercially available or may be prepared by any suitable means, including bulk, solution, and emulsion polymerization.

The compositions of the present invention can be prepared by mixing a solution of the biologically active compound with a solution of the hydroxystyrene polymer. In the alternative, either the biologically active compound or the hydroxystyrene polymer may be added neat to a solution of the other component. For example, a hydroxystyrene polymer may be added neat to a solution of the biologically active compound. The solvent can be removed by any means, such as under reduced pressure, to yield a solid or liquid composition. The solvent used to dissolve the biologically active compound may be the same or different from that used to dissolve the hydroxystyrene polymer. When different solvents are used to dissolve the biologically active compound and the hydroxystyrene polymer, it is preferred that they be miscible with each other. Mixtures of solvents may also be used. Suitable solvents include alcohols, such as methanol, ethanol, and propanol; esters, such as ethyl acetate and butyl acetate; ketones, such as acetone and methyl iso-butyl ketone; nitriles, such as acetonitrile; and the like. In the alternative, either the biologically active compound or the hydroxystyrene polymer or both may be blended as a melt. When a melt is used to prepare the compositions of the present invention, it is preferred that the biologically active compound is melted and the hydroxystyrene polymer combined with the melt. When the compositions of the present invention are oils, it is preferred that they be taken up in a carrier.

The hydroxystyrene polymers of the present invention may be loaded with generally from 0.1%wt to 95%wt of the biologically active compound, based on the weight of the hydroxystyrene polymer. Thus, the weight ratio of biologically active compound to hydroxystyrene polymer in the compositions is generally from 0.1:99.9 to 95:5. Preferably, the weight ratio is from 1:10 to 9:1 and more preferably from 1:3 to 4:1.

More than one biologically active compound may be used in the compositions of the present invention as long as the compounds do not irreversibly react with, or otherwise destabilize, each other and are compatible with the hydroxystyrene polymer. This has the advantage of controlling the release of multiple biologically active compounds which may provide a broader spectrum of control than one compound alone. Also, this may reduce the cost of treatment when multiple biologically active compounds must be used. When more than one biologically active compound is used, the ratio of the total amount of the biologically active compounds to the hydroxystyrene polymer is generally from 0.1:99.9 to 95:5.

The compositions of the invention may further comprise a carrier, such as water, organic solvent or mixtures thereof. Suitable organic solvent carriers include, but are not limited to: acetonitrile, ethyl acetate, butyl acetate, toluene, xylene, methanol, ethanol, acetone, methyl ethyl ketone, methyl isobutyl ketone, ethylene glycol, diethylene glycol, propylene glycol, dipropylene glycol, and glycol ethers. When the compositions of the invention are to be used in an agricultural application, it is preferred that the carrier be an agronomically acceptable carrier.

The compositions of the invention are useful wherever the biologically active compound would be useful. When the biologically active compound is a microbicide, the compositions of the invention are useful in controlling or inhibiting the growth of microorganisms, such as bacteria and fungi, in a locus. The compositions of the invention are suitable for use in any locus requiring protection from microorganisms. Suitable loci include, but are not limited to: cooling towers; air washers; mineral slurries; pulp and paper processing fluids; paper coatings; swimming pools; spas; adhesives; caulks; mastics; sealants; agriculture adjuvant preservation; construction products; cosmetics and toiletries; shampoos; disinfectants and antiseptics; formulated industrial and consumer products; soaps; laundry rinse waters; leather and leather products; wood, including lumber, timber, fiberboard, plywood, and wood composites; plastics; lubricants; hydraulic fluids; medical devices; metalworking fluids; emulsions and dispersions; paints, including marine paints; varnishes, including marine varnishes; latexes; odor control fluids; coatings, including marine coatings; petroleum processing fluids; fuel; oil field fluids; photographic chemicals; printing fluids; sanitizers; detergents; textiles, such as fibers; and textile products, such as clothes and carpets.

When compositions of the invention comprise a microbicide, they can either be added directly to the locus to be protected or added as a composition further comprising a suitable carrier. Suitable carriers useful for microbicidal applications include, but are not limited to, water; organic solvent, such as ethylene glycol, diethylene glycol, propylene glycol, dipropylene glycol, xylene, toluene, acetone, methyl iso-butyl ketone, or esters; or mixtures thereof. The compositions may also be formulated as microemulsions, microemulsifiable concentrates, emulsions, emulsifiable concentrates, pastes, or may be encapsulated. The particular formulation will depend upon the locus to be protected and the particular microbicide used. The preparation of these formulations is by well known, standard methods.

When the compositions comprise a microbicide, the amount of the compositions of the invention necessary to control or inhibit the growth of microorganisms depends upon the locus to be protected, but is typically sufficient if it provides from 0.5 to 2500 ppm of microbicide, at the locus to be protected. Microbicides are often used in loci that require further dilution. For example, the compositions of the invention may be added to a metal working fluid concentrate, which is then further diluted. The amounts of the compositions of the invention necessary to control microorganism growth in the final metal working fluid dilution are sufficient if they provide generally from 5 to 50 ppm of the microbicide in the final dilution. In loci such as a paint, which is not further diluted, the amount of the compositions of the invention necessary to control microorganism growth are sufficient if they provide generally from 500 to 2500 ppm of the microbicide.

When the biologically active compound of the present invention is a marine antifouling agent, the compositions of the present invention can be used to inhibit the growth of marine organisms by application of the compositions onto or into a marine structure. Depending upon the particular marine structure to be protected, the compositions of the present invention can be directly incorporated into the marine structure, applied directly to the marine structure, or incorporated into a coating which is then applied to the marine structure.

Suitable marine structures include, but are not limited to: boats, oil platforms, piers, pilings, docks, elastomeric rubbers, and fish nets. The compositions of the present invention are typically directly incorporated into structures such as elastomeric rubber or fish net fibers during manufacture. Direct application of the compositions of the invention is typically made to structures such as fish nets or wood pilings. The compositions of the invention can also be incorporated into a marine coating, such as a marine paint or varnish.

When the compositions of the invention comprise a marine antifouling agent, the amount of the compositions of the invention necessary to inhibit or prevent the growth of marine organisms is typically sufficient if it provides from 0.1 to 30%wt of marine antifouling agent alone, based on the weight of the structure to be protected or based on the weight of the coating to be applied. When the compositions of the invention are directly incorporated into or directly applied onto a structure, the amount of the compositions necessary to inhibit the growth of marine organisms is generally sufficient if it provides 0.1 to 30%wt of marine antifouling agent alone, based on the weight of the structure. It is preferred that the amount of the compositions of the invention be sufficient to provide 0.5 to 20%wt of marine antifouling agent alone; more preferably, 1 to 15%wt. When incorporated into a coating, the amount of the compositions of the invention suitable to inhibit the growth of marine organisms is generally sufficient if it provides 0.1 to 30%wt of marine antifouling agent alone, based on the weight of said coating. The amount of the compositions of the invention preferably provides 0.5 to 15%wt of marine antifouling agent alone; more preferably, 1 to 10%wt.

In general, the compositions of the invention comprising a marine antifouling agent are incorporated in a carrier such as water; organic solvent, such as xylene, methyl isobutyl ketone, and methyl isoamyl ketone; or mixtures thereof.

Direct applications of the compositions of the invention may be by any conventional means, such as dipping, spraying, or coating. Fish nets, for example, may be also protected by dipping the fish nets into a composition comprising the compositions of the invention and a carrier or by spraying the fish nets with said composition.

Structures such as wood pilings and fish nets may be protected by directly incorporating the compositions of the invention into the structure. For example, a composition of the invention further comprising a carrier may be applied to wood used for pilings by means of pressure treatment or vacuum impregnation. These compositions may also be incorporated into a fish net fiber during manufacture.

Marine coatings comprise a binder and solvent and optionally other ingredients. The solvent may be either organic solvent or water. The compositions of the invention are suitable for use in both solvent- and water-based marine coatings. Solvent-based marine coatings are preferred.

Any conventional binder may be utilized in the marine antifouling coating incorporating the compositions of the invention. Suitable binders include, but are not limited to: polyvinyl chloride in a solvent-based system; chlorinated rubber in a solvent based system; acrylic resins in solvent-based or aqueous systems; vinyl chloride-vinyl acetate copolymer systems as aqueous dispersions or solvent-based systems; butadiene-styrene rubbers; butadiene-acrylonitrile rubbers; butadiene-styrene-acrylonitrile rubbers; drying oils such as linseed oil; asphalt; epoxies; siloxanes; and the like.

The marine coatings of the present invention may optionally contain one or more of the following: inorganic pigments, organic pigments, or dyes, and controlled release materials, such as rosin. Water-based coatings may also optionally contain: coalescents, dispersants, surface active agents, rheology modifiers, or adhesion promoters. Solvent-based coatings may also optionally contain extenders, plasticizers, or rheology modifiers.

A typical marine coating comprises 2 to 20%wt binders, up to 15%wt rosins/modified rosins, 0.5 to 5%wt plasticizers, 0.1 to 2%wt antisettling agent, 5 to 60%wt solvent/diluent, up to 70%wt cuprous oxide, up to 30%wt pigments (other than cuprous oxide), and up to 15%wt marine antifouling agent.

Marine coatings containing the compositions of the invention may be applied to a structure to be protected by any of a number of conventional means. Suitable means of application include, but are not limited to, spraying; rolling; brushing; or dipping.

When the biologically active compound is an agricultural pesticide, the compositions of the invention may be applied to plants or soil or may be used as seed treatments. The compositions may be used directly or formulated as dusts, granules, flowables, emulsifiable concentrates, microemulsifiable concentrates, emulsions, microemulsions, or may be encapsulated.

The following examples are presented to illustrate further various aspects of the present invention, but are not intended to limit the scope of the invention in any aspect.

EXAMPLE 1

The following are examples of compositions of the present invention prepared according to the following general method.

A solution of the hydroxystyrene polymer in methanol or ethyl acetate was placed in a flask. To this solution was added a solution of 4,5-dichloro-2-n-octyl-3-isothiazolone in the same solvent as the hydroxystyrene polymer. The amount of the 4,5-dichloro-2-n-octyl-3-isothiazolone added was such that the final product contained from 25–80%wt of the 4,5-dichloro-2-n-octyl-3-isothiazolone, based on the weight of the composition. After thorough mixing, the solvent was then removed in vacuo at 55° C. to yield an oil. The yields of the final products were 95–100%. Samples 2–5 were then taken up in methyl iso-butyl ketone to give a solution.

Hydroxystyrene Polymer

A=hydroxystyrene/styrene block copolymer, $M_w$(hydroxystyrene block)=10656; $M_w$(styrene block)=6156

B=hydroxystyrene homopolymer, $M_w$=5200, $M_n$=2700

C=hydroxystyrene homopolymer, $M_w$=28,300

D=hydroxystyrene/styrene copolymer, $M_w$=2600, $M_n$=1700

TABLE 1

Compositions of the Invention

| Sample | Hydroxystyrene Polymer (% wt) | 4,5-Dichloro-2-n-octyl-3-isothiazolone (% wt) | Physical State |
|---|---|---|---|
| 1 | A (75) | 25 | Oil |
| 2 | B (40) | 60 | Oil |
| 3 | B (20) | 80 | Oil |
| 4 | C (40) | 60 | Oil |
| 5 | D (40) | 60 | Oil |

EXAMPLE 2

The compositions of Example 1 were evaluated for their rate of release of biologically active compound according to the following procedures.

An amount of Sample 1 sufficient to provide 20 mg/L of 4,5-dichloro-2-n-octyl-3-isothiazolone if all the 4,5-dichloro-2-n-octyl-3-isothiazolone were released was weighed into a 100 mL glass jar. To this solution was added 100 mL of DI water containing 0.3%wt of sodium dioctyl sulfosuccinate as surfactant. The solution was then gently stirred. Aliquots (0.5 mL) were taken at various time points and placed in a micro centrifuge tube and centrifuged at 14,000 rpm for 3 minutes. The resultant clear aqueous layer was then analyzed for 4,5-dichloro-2-n-octyl-3-isothiazolone. The centrifuge tube was then washed with 0.5 ml of fresh water/surfactant solution and the wash solution was then returned to the glass jar. This ensured that none of the particles removed during sampling were lost and that the volume stayed constant. The aliquots were analyzed by HPLC for the amount of 4,5-dichloro-2-n-octyl-3-isothiazolone released. The cumulative percentages of 4,5-dichloro-2-n-octyl-3-isothiazolone ported in Table 2.

TABLE 2

% of 4,5-Dichloro-2-n-octyl-3-isothiazolone Released

| Sample | 4 Days | 7 Days | 10 Days |
|---|---|---|---|
| 1 | 5 | 6 | 7 |

From these data, it can be clearly seen that the compositions of the present invention slowly release the 4,5-dichloro-2-n-octyl-3-isothiazolone over a period of days.

EXAMPLE 3

The compositions of Example 1 were evaluated for the control of the release of biologically active molecules in a marine paint.

A blank paint, that is one that contained no biologically active molecules, was dosed with Samples 2–5. The amount of the samples added was such that the total amount of 4,5-dichloro-2-octyl-3-isothiazolone in the paint was 5%wt, based on the total weight of the dry paint film. A control paint was prepared by adding 4,5-dichloro-2-octyl-3-isothiazolone alone. Glass slides were painted with the treated paints as well as the control paint and allowed to dry in a hood for 6 days. The slides were then submerged in a tank of synthetic sea water. The slides were removed after 14 days and the paint film extracted. The extracts were analyzed by HPLC to determine the amount of 4,5-dichloro-2-octyl-3-isothiazolone remaining. The amount of 4,5-dichloro-2-octyl-3-isothiazolone released from the paints is reported in Table 3.

TABLE 3

% of 4,5-Dichloro-2-n-octyl-3-isothiazolone Released

| Sample | 14 Days |
|---|---|
| 2 | 22.6 |
| 3 | 7.2 |
| 4 | 10.4 |
| 5 | 26.3 |
| Control | 29.0 |

The above data clearly show that the controlled release compositions of the present invention release 4,5-dichloro-2-octyl-3-isothiazolone from a dry paint film more slowly as compared to the control.

What is claimed:

1. A controlled release composition comprising a mixture of a biologically active compound and a hydroxy styrene polymer; wherein the biologically active compound is selected from the group consisting of 5-chloro-2-methyl-3-isothiazolone; 2-methyl-3-isotiazolone; 2-n-octyl-3-isothiaolone; 4,5-dichloro-2-n-octyl-3-isothiazolone; 1,2-dibromo-2,4-dicyanobutane; methylene-bis-thiocyanate; 2-thiocyanomethyl thiobenzothiazole; tetrachloroisophthalonitrile; 5-bromo-5-nitro-1,3-dioxane; 2-bromo-2-nitropropanediol; 2,2-dibromo-3-nitrilopropionamide; N,N-dimethylhydroxy-5,5'-dimethylhydantoin; bromochlorodimethylhydantoin; 1,2-benzisothiaolin-3-one; 4,5-trimethylene-2-methyl-3-isothiazolone; 5-chloro-2-(2,4-dichlorophenoxy)phenol; 3,4,4'-trichlorocarbanilide; manganese ethylene-bis-dithiocarbamate; zinc dimethyl dithiocarbamate; 2-methyl-4-t-butyl amino-6-cyclopropyl amino-s-triazine; 2,4,5,6-tetrachloro isophthalonitrile; N,N-dimethyl dichloro phenyl urea; zinc ethylene-bis-dithiocarbamate; copper thiocyanate; N-(fluorodichloromethylthio)-phthalimide; N,N-dimethyl-N'-phenyl-N'-fluorodichloromethylthio-sulfamide; zinc 2-pyridine thiol-1-oxide; tetramethylthiuram disulfide; 2,4,6-trichlorophenylmaleimide; 2,3,5,6-tetrachloro-4-(methyl sulfanyl)-pyridine; 3-iodo-2-propynyl butyl carbamate; bis-dimethyl dithio carbamoyl zinc ethylene-bis-dithiocarbamate; phenyl (bispyridil) bismuth dichloride; 2-(4-thiazolyl)-benzimidazole; pyridine triphenyl borane; phenyl amides; halo propargyl compounds; 2-haloalkoxyaryl-3-isothiazolones and combinations thereof; and wherein the weight ratio of biologically active compound to hydroxystyrene polymer, is from 1:10 to 9:1.

2. The composition of claim 1 wherein the hydroxystyrene polymer is a copolymer of hydroxystyrene and one or more monoethylenically unsaturated monomers.

3. The composition of claim 2 wherein the monoethylenically unsaturated monomer is selected from the group consisting of vinylaromatic monomers, nitrogen-containing ring compounds, ethylene and substituted ethylene monomers.

4. The composition of claim 1 wherein the hydroxy styrene polymer is selected from the group consisting of hydroxy styrene homopolymer, hydroxy methyl styrene homopolymer, halo hydroxy styrene homopolymer, hydroxy styrene/styrene copolymer, hydroxy styrene/methyl methacrylate copolymer, hydroxy styrene/butyl acrylate copolymer and hydroxy styrene/hydroxyethyl methacrylate.

5. The composition of claim 1 further comprising a carrier selected from the group consisting of water, acetonitrile, ethyl acetate, butyl acetate, toluene, xylene, methanol, ethanol, acetone, methyl ethyl ketone, methyl iso-butyl ketone, ethylene glycol, diethylene glycol, propylene glycol, and dipropylene glycol.

6. The composition of claim 1 wherein the weight ratio of biologically active compound to hydroxystyrene polymer is from 1:3 to 4:1.

7. A method for controlling or inhibiting the growth of fungi, bacteria, algae, marine fouling organisms, plants, and insects comprising introducing a composition of claim 1 to a locus to be protected.

8. The method of claim 7 wherein the locus to be protected is selected from: cooling towers; air washers; mineral slurries; pulp and paper processing fluids; paper coatings; adhesives; caulks; mastics; sealants; agriculture adjuvant preservation; construction products; cosmetics and toiletries; shampoos; disinfectants and antiseptics; formulated industrial and consumer products; soaps; laundry rinse waters; leather and leather products; wood; plastics; lubricants; hydraulic fluids; medical devices; metalworking fluids; emulsions and dispersions; paints; varnishes; latexes; odor control fluids; coatings; petroleum processing fluids; fuel; oil field fluids; photographic chemicals; printing fluids; sanitizers; detergents; textiles; textile products; marine structures; plants; soil; and seeds.

9. The method according to claim 7 wherein the composition contains at least 0.5 ppm of a microbiocide selected from the group consisting of 2-methyl-3-isothiazolone, 5-chloro-2-methyl-3-isothiazolone, 2-n-octyl-3-isothiazolone, 4,5-dichloro-2-n-octyl-3-isothiazolone, benzisothiazolone, 4,5'-trimethylene-3-isothiazolone, 3-iodo-2-propynyl butyl carbamate; 5-chloro-2-(2,4-dichlorophenoxy)phenol and 3,4,4'-trichlorocarbanilide.

10. The method according to claim 9 wherein the ratio of microbiocide to hydroxy styrene polymer is from 1:3 to 4:1.

11. The method according to claim 9 wherein the composition is a marine anti-fouling composition containing one or more microbiocides in an amount from 0.1 to 30 weight percent, based on the weight of a marine structure to be protected or based on the weight of a coating applied to the marine structure.

12. A composition for controlling or inhibiting the growth of marine fouling organisms comprising a mixture of a marine anti-fouling agent and a hydroxy styrene polymer; wherein the marine anti-fouling agent consists of at least one isothiazolone compound and wherein from 0.1 to 30 weight percent of the anti-fouling agent is incorporated in a paint or a coating applied to a marine structure, based on the weight of the hydroxy styrene polymer or based on the weight of the structure.

13. The composition according to claim 12 wherein the hydroxy styrene polymer is selected from the group consisting of hydroxy styrene homopolymer, hydroxy methyl styrene homopolymer, halo hydroxy styrene homopolymer, hydroxy styrene/styrene copolymer, hydroxy styrene/methyl methacrylate copolymer, hydroxy styrene/butyl acrylate copolymer and hydroxy styrene/hydroxyethyl methacrylate.

14. The composition according to claim 13 wherein the isothiazolone compound is selected from the group consisting of 5-chloro-2-methyl-3-isothiazolone; 2-methyl-3-isothiazolone; 2-n-octyl-3-isothiazolone; benzisothiazolone; 4,5-dichloro-2-n-octyl-3-isothiazolone; 4,5-dichloro-2-n-octyl-3-isothiazolone; 1,2-benzisothiazolin-3-one; 4,5-trimethylene-2-methyl-3-iosthia-zolone, 2-haloalkoxyaryl-3-isothiazolones such as 2-(4-trifluoro methoxy phenyl)-3-isothiazolone, 2-(4-trifluoro methoxy phenyl)-5-chloro-3-isothiazolone, and 2-(4-trifluoro methoxy phenyl)-4,5-dichloro-3-isothiazolone and combinations thereof.

15. The composition according to claim 14 wherein the weight ratio of anti-fouling agent to hydroxy styrene polymer is from 1:3 to 4:1.

16. The composition according to claim 14 wherein the marine structure is selected from the group consisting of boats, oil platforms, piers, pilings, docks, elastomeric rubbers, and fish nets.

17. The composition according to claim 14 wherein the composition optionally contains additional anti-fouling agents selected from the group consisting of manganese ethylene bis dithiocarbamate; zinc dimethyl dithiocarbamate; 2-methyl-4-t-butyl amino-6-cyclopropyl amino-s-triazine; 2,4,5,6-tetrachloro isophthalonitrile; N,N-dimethyl dichloro phenyl urea; zinc ethylene bis dithiocarbamate; copper thiocyanate; N-(fluoro dichloro methyl thio) phthalimide; N,N-dimethyl-N'-phenyl-N'-fluoro dichloro methyl thio-sulfamide; zinc 2-pyridine thiol-1-oxide; tetramethyl thiuram disulfide; 2,4,6-trichloro phenyl maleimide; 2,3,5,6-tetrachloro-4-(methyl sulfonyl)-pyridine; 3-iodo-2-propynyl butyl carbamate; diiodomethyl p-tolyl sulfone; bis dimethyl dithio carbamoyl zinc ethylene bis dithiocarbamate; phenyl (bispyridil) bismuth dichloride; 2-(4-thiazolyl)-benzinmidazole; pyridine triphenyl borane; phenyl amides; halo propargyl compounds and combinations thereof.

18. The composition according to claim 14 wherein the composition optionally contains at least one anti-fouling agent as a metal salt.

* * * * *